(12) United States Patent
Alici

(10) Patent No.: US 8,877,182 B2
(45) Date of Patent: Nov. 4, 2014

(54) EXPANSION OF NK CELLS

(75) Inventor: Evren Alici, Gnesta (SE)

(73) Assignee: Cellprotect Nordic Pharmaceuticals AB, Huddinge (SE)

( * ) Notice: Subject to any disclaimer, the term of this patent is extended or adjusted under 35 U.S.C. 154(b) by 38 days.

(21) Appl. No.: 13/260,004

(22) PCT Filed: Mar. 25, 2010

(86) PCT No.: PCT/SE2010/050333
§ 371 (c)(1),
(2), (4) Date: Jun. 22, 2012

(87) PCT Pub. No.: WO2010/110734
PCT Pub. Date: Sep. 30, 2010

(65) Prior Publication Data
US 2012/0258085 A1   Oct. 11, 2012

Related U.S. Application Data

(60) Provisional application No. 61/163,590, filed on Mar. 26, 2009.

(51) Int. Cl.
*A61P 35/00* (2006.01)
*C12N 5/0783* (2010.01)
*A61K 35/14* (2006.01)

(52) U.S. Cl.
CPC .......... *C12N 5/0646* (2013.01); *C12N 2501/23* (2013.01); *C12N 2501/515* (2013.01); *C12N 2501/2302* (2013.01)
USPC ........................................ 424/93.71; 435/372

(58) Field of Classification Search
CPC ...................... C12N 2501/2302; C12N 5/0646; C12N 2501/515; C12N 2501/23
USPC ........................................ 424/93.71; 435/372
See application file for complete search history.

(56) References Cited

U.S. PATENT DOCUMENTS

| 2003/0068306 A1 | 4/2003 | Dilber |
| 2003/0119185 A1* | 6/2003 | Berenson et al. ............. 435/372 |
| 2009/0123442 A1* | 5/2009 | Dilber et al. ............... 424/93.71 |

FOREIGN PATENT DOCUMENTS

| WO | 01/37671 A1 | 5/2001 |
| WO | 2006/072625 A2 | 7/2006 |

(Continued)

OTHER PUBLICATIONS

GE Healthcare Life Sciences, Perfusion culture of human natural killer cells in the WAVE Bioreactor™ 2/10 system, 2011, Available online at: promo.gelifesciences.com/GL/XURI/ misc/ litdoc28993625AA_20110901000155.pdf.*

(Continued)

*Primary Examiner* — Karen Cochrane Carlson
*Assistant Examiner* — Jennifer M. H. Tichy
(74) *Attorney, Agent, or Firm* — Porter Wright Morris & Arthur LLP

(57) ABSTRACT

A method of obtaining expanded and activated natural killer (NK) cells with the phenotype CD3⁻CD56⁺ and NK-like T cells with the phenotype CD3⁺CD56⁺ comprises providing a cell sample of peripheral blood from a tumor bearing subject; isolating cells from the blood sample and re-suspending the cells in growth medium; adding the isolated cells to a closed cell culture bag bioreactor at a concentration of about $0.5 \times 10^6$ to about $2 \times 10^6$/ml of growth medium; incubating and expanding the cells of step ii) with rocking motion agitation and heating until at least 50% of the expanded cell population comprises activated NK cells and NK-like T cells; and harvesting the expanded cell suspension of therapeutically active NK-cells and NK-like T cells from the bioreactor, wherein the cells exhibit an increased cytotoxicity compared to freshly isolated cells as determined by an in vitro cytotoxicity test.

27 Claims, 14 Drawing Sheets

(56) References Cited

FOREIGN PATENT DOCUMENTS

| WO | 2009060865 A1 | 5/2009 |
|---|---|---|
| WO | 2009/151183 A1 | 12/2009 |

OTHER PUBLICATIONS

Laiuppa et al., Culture materials affect ex vivo expansion of hematopoietic progenitor cells, Journal of Biomed. Mater. Res. 1997, 36:347-359.

Nielsen, Bioreactors for Hematopoietic Cell Culture, Annu. Rev. Biomed. Eng. 1999, 01:129-152.

Biassoni et al., Human Natural Killer Receptors and Their Ligands, Current Protocals in Immunology 2001, Supplement 46, 14.10.1-14.10.23.

Heiskala et al., Mechanism of Cell Contact-Mediated Inhibition of Natural Killer Activity, The Journal of Immunology, 1987 vol. 139, No. 5, 1414-1418.

Ramsdell et al., Generation of Lymphokine-Activated Killer Cell Activity From Human Thymocytes, The Journal of Immunology, 1987, vol. 139, No. 5, 1446-1453.

Sutlu et al., Natural killer cell-based immunotherapy in cancer: current insights and future prospects, Journal of Internal Medicine, 2009, 266:154-181.

Chan et al., Enhanced Killing of Primary Ovarian Cancer by Retargeting Autologous Cytokine-Induced Killer Cells with Bispecific Antibodies: A Preclinical Study, Clinical Cancer Research 2006; 12:1859-1867.

Guimaraes et al., Evaluation of ex vivo expanded human NK cells on antileukemia activity in SCID-beige mice, Leukemia, 2006; 20:833-839.

Ishikawa et al., Autologous Natural Killer Cell Therapy for Human Recurrent Malignant Glioma, Anticancer Research, 2004; 24: 1861-1872.

Khalil-Daher et al., Role of HLA-G versus HLA-E on NK function: HLA-G is able to inhibit NK cytolysis by itself, Journal of Reproductive Immunology, 1999; 43: 175-182.

Klingemann et al., Ex vivo expansion of natural killer cells for clinical applications, Cytotherapy, 2004; vol. 6, No. 1: 15-22.

Vitale et al., NKp44, a Novel Triggering Surface Molecule Specifically Expressed by Activated Natural Killer Cells, Is Involved in Non-Major Histocompatibility Complex-restricted Tumor Cell Lysis, J. Exp. Med. 1998; vol. 187, No. 12: 2065-2072.

Lu et al., A Novel Population of Expanded Human CD3+CD56+ Cells Derived from T Cells with Potent In Vivo Antitumor Activity in Mice with Severe Combined Immunodeficiency, The Journal of Immunology, 1994; 153:1687-1696.

Barkholt, et al., Safety analysis of ex vivo-expanded NK and NK-like T cells administered to cancer patients: a Phase I clinical study, Immunotherapy, 2009; 1(5):753-764.

Alter et al., CD107a as a functional marker for the identification of natural killer cell activity, Journal of Immunological Methods, 2004; 294:15-22.

Torelli et al., Expansion of natural killer cells with lytic activity against autologous blasts from adult and pediatric acute lymphoid leukemia patients in complete hematologic remission, Haematologica/The Hemotology Journal, 2005; 90(6):785-792.

Bordignon, et al., Cell therapy: achievements and perspectives, Haematologica, 1999; 84(12):1110-1149.

Grimm et al., Lymphokine-Activated Killer Cell Phenomenon Lysis of Natural Killer-resistant Fresh Solid Tumor Cells by Interleukin 2-activated Autologous Human Peripheral Blood Lymphocytes, Journal of Experimental Medicine, 1982, vol. 155, 1823-1841.

Carlens et al., A New Method for In Vitro Expansion of Cytotoxic Human CD3-CD56+ Natural Killer Cells, Human Immmunology 2001, 62:1092-1098.

Meehan et al., Development of a clinical model for ex vivo expansion of multiple populations of effector cells for adoptive cellular therapy, Cytotherapy, 2008, 10(1):30-37.

Guven et al., Expansion of natural killer (NK) and natural killer-like T (NKT)-cell populations derived from patients with B-chronic lymphocytic leukemia (B-CLL): a potential source for cellular immunotherapy, Leukemia, 2003, vol. 17 1973-1980.

Alici et al., Autologous antitumor activity by NK cells expanded from myeloma patients using GMP-compliant components, Blood, 2008, vol. 111, No. 6, 3155-3162.

Arai et al., Infusion of the allogeneic cell line NK-92 in patients with advanced renal cell cancer or melanoma: a phase I trial, Cytotherapy, 2008, vol. 10, No. 6, 625-632.

Tam et al., Ex vivo expansion of the highly cytotoxic human natural killer cell line NK-92 under current good manufacturing practice conditions for clinical adoptive cellular immunotherapy, Cytotherapy, 2003, vol. 5, No. 3, 259-272.

Luhm et al., Large-Scale Generation of Natural Killer Lymphocytes for Clinical Application, Journal of Hematotherapy & Stem Cell Research, 2002, 11:651-657.

Pierson et al., Production of Human Natural Killer Cells for Adoptive Immunotherapy Using Computer-Controlled Stirred-Tank Bioreactor, Journal of Hematotherapy, 1996, 5:475-483.

Carlens et al, A New Method for In Vitro Expansion of Cytotoxic Human CD3-CD56+ Natural Killer Cells, Human Immunology 62:1092-1098 (2001).

Knazek et al, Culture of human tumor infiltrating lymphocytes in hollow fiber bioreactors, Journal of Immunological Methods, 127, (1990), 29-37.

Carswell et al, Culture of Human T Cells in Stirred Bioreactors for Cellular Immunotherapy Applications: Shear, Proliferation, and the IL-2 Receptor, Biotechnology and Bioengineering, 68(3): 328-338 (2000).

Hillman et al, Expansion of Activated Lymphocytes Obtained from Renal Cell Carcinoma in an Automated Hollow Fiber Bioreactor, Cell Transplantation, vol. 3, No. 4, 1994, pp. 263-271.

Hillman et al, Adoptive immunotherapy of cancer: biological response modifiers and cytotoxic cell therapy, Biotherapy 5, 1992, pp. 119-129.

English Translation of Official Action dated Aug. 5, 2014 from corresponding Japanese Application No. 2012-501965.

* cited by examiner

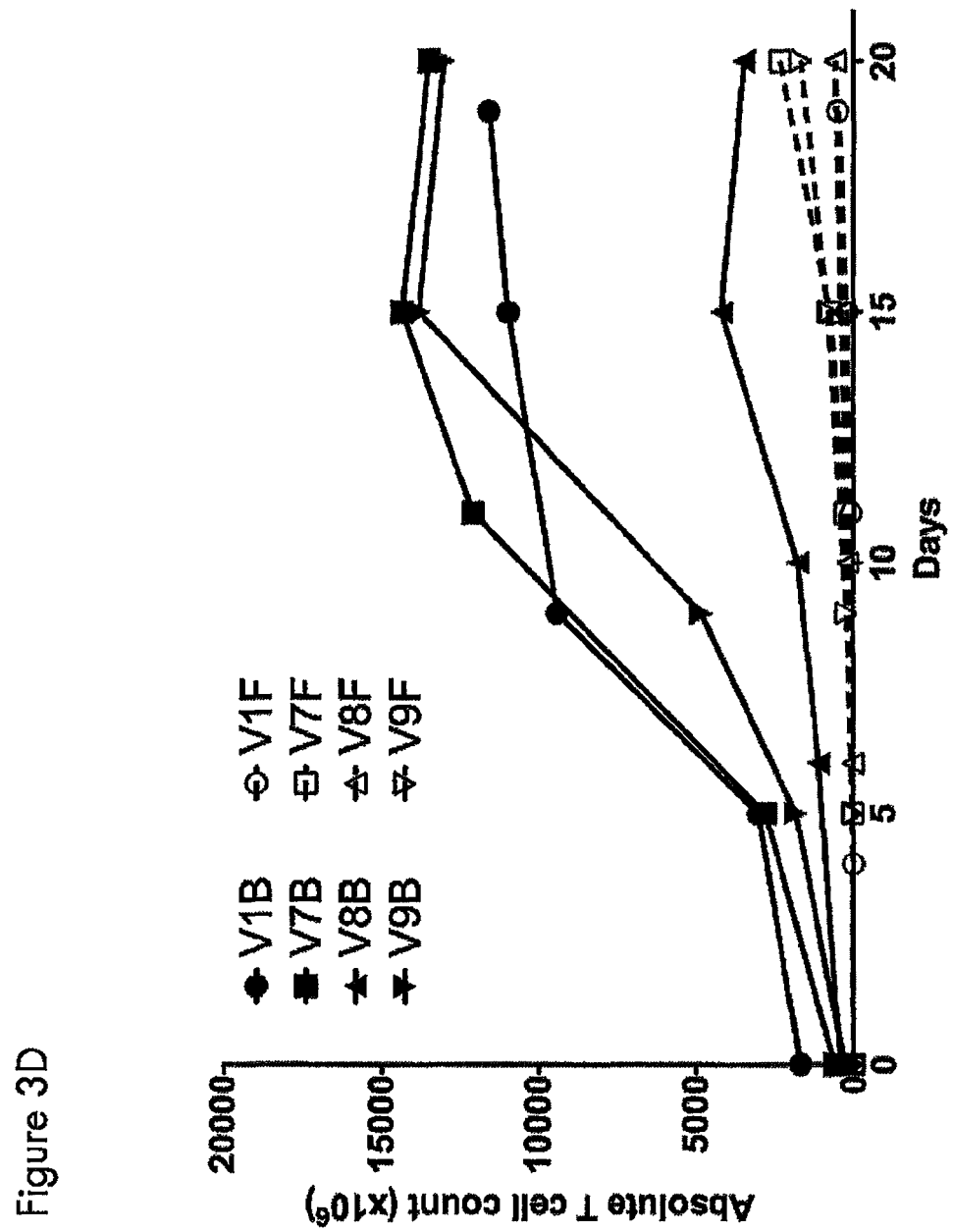

EXPANSION OF NK CELLS

RELATED APPLICATION

The present application is a 371 of PCT/SE2010/050333 filed Mar. 25, 2010 and claims priority under 35 U.S.C. 119 of U.S. Application No. 61/163,590 filed Mar. 26, 2009.

TECHNICAL FIELD

The present invention relates to cell culture and immunotherapy, in particular large scale expansion and simultaneous activation of NK cells and NK-like T cells for therapeutic uses. The cells are expanded in a closed automated culture system, for example using a bioreactor.

BACKGROUND OF THE INVENTION

The use of cellular immunotherapy against cancer has been thoroughly investigated since the introduction of lymphokine-activated killer (LAK) cells in the mid-1980s (Grimm E A. et al., 1982; Rosenberg S., 1985).

One of the most experimented approaches has been adoptive transfer of autologous or allogeneic cytotoxic effectors with tumor cell killing potential to trigger a graft-vs-tumor (GvT) effect. Among the various effector populations that have a potential anti-tumor effect, natural killer (NK) and NK-like T cells stand out with their high cytotoxic capacity (Sutlu T and Alici E., 2009).

NK and NK-like T cells are normally present only in low numbers in peripheral blood mononuclear cells (PBMCs) and effector cell preparations such as LAK cells. Therefore methods involving current good manufacturing practice (cGMP)-compliant components that allow expansion of polyclonal NK cells and NK-like T cells in cell culture flasks using PBMCs from healthy donors (Carlens S. et al., 2001 and U.S. Ser. No. 10/242,788), as well as patients with B-cell chronic lymphocytic leukemia (Guven H. et al., 2003), and multiple myeloma (MM) (Alici E. et al., 2008) have been developed. These cells have been shown to exert specific cytotoxic activity against fresh human tumor cells in vitro and in experimental models of human tumors (Guimaraes F. et al., 2006) which opens up the possibility to be evaluated in clinical settings. However, the conventional flask-based culture is labor-intensive and cumbersome, thus limiting the cell number that can be handled practically. Previously disclosed protocols (e.g. Miller J S. et al., 1994; Pierson B A. et al., 1996; Luhm J. et al., 2002; Klingermann H G and Martinson J., 2004) directed to effector cell preparation also include steps such as NK precursor or CD56 separation prior to culture and the use of feeder cells or cGMP-incompatible components. These disadvantages render previous protocols suboptimal and unfeasible to support large clinical studies.

Furthermore, expansion of NK cells in cell culture flasks has the inherent risk of exposure to external agents and contamination. Although this risk is minimized in GMP laboratory environments, the use of closed automated systems is definitely preferred as long as it supplies sufficient amounts of cells.

Since hematopoietic cells are relatively sensitive to shear it is reasonable to assume that high shear processes are unsuitable for ex vivo expansion (Nielsen, 1999). Thus, stirred-tank bioreactors (Pierson. et al., 1996) or perfusion culture systems relying on external filters and high flow rate are unlikely to provide a high efficiency.

There are many promising approaches for the treatment of cancer with NK cell and NK-like T cell based immunotherapy. However, ex vivo expansion and activation of these effector cells under GMP compatible closed systems are crucial factors for facilitating frequent clinical use.

There have also been attempts by other investigators to expand and/or activate NK cells ex vivo and treatment options using purified/resting, short term or highly purified and long term activated NK cells are being investigated. These studies report NK cell infusions to be well tolerated and partially effective. Yet, the protocols used for effector cell preparation commonly include additional steps such as NK precursor or CD56 separation prior to culture and the use of feeder cells and/or cGMP-incompatible components. These disadvantages render such protocols suboptimal for GMP production and unfeasible for supporting large clinical studies.

A thorough evaluation of the above-mentioned reports shows a need for an automated method for optimized ex vivo expansion of NK cells. One problem with conventional flask-based cultures is related to scale, i.e. the cell number is limited due to the cumbersome handling of the flasks. Further, the risk of infections is quite high since the system is exposed to the environment each time the media are changed or the cells split. Further problems to be solved involve developing a method for the expansion of effector cells which is cost-effective, easy to handle and which includes well-defined cGMP quality components. Preferably the culture system is also free of animal products and feeder cells.

SUMMARY OF INVENTION

The present invention relates to a closed system for large scale expansion and simultaneous activation of natural killer (NK) cells and NK-like T-cells, to be used as cell therapy products. In particular the invention discloses a method for large scale expansion and simultaneous activation of NK cells with the phenotype $CD3^-CD56^+$ and NK-like T cells with the phenotype $CD3^+ CD56^+$, wherein the expanded cells exhibit increased cytotoxicity compared to cells cultured using conventional methods, such as flasks, under the same or similar conditions. The inventive method will be further disclosed in the description, non-limiting examples, and claims.

The inventors have investigated the feasibility of large-scale NK cell expansion using closed systems. Two different closed systems (cell culture bags and an automated bioreactor) have been evaluated in comparison to conventional cell culture flasks using PBMCs from healthy donors and patients with MM, with the aim of developing an automated GMP-compatible protocol that allows large-scale production of NK cells to be used for immunotherapy.

Concurrently, the inventors have successfully completed a safety evaluation of this cell product in an allogeneic setting in a phase I clinical trial with cancer patients (Barkholt L. et al., 2009).

According to a first embodiment of the present invention, a method for large scale expansion and simultaneous activation of certain cell types is provided, wherein a closed cell culture system is used, and wherein the expanded cells obtained by this method exhibit an increased cytotoxicity as determined by in vitro cytotoxicity tests. Preferably the cell types are natural killer (NK) cells with the phenotype $CD3^-CD56^+$ and/or NK-like T cells with the phenotype $CD3^+CD56^+$.

According to a preferred embodiment the method comprises the steps of adding said cells to said closed system comprising a growth medium supplemented with serum, interleukin-2 (IL-2) and anti-CD3 antibodies; expanding said cells within said system with agitation and heating until: at least 35% of the expanded cell population comprises activated NK cells and NK-like T cells, and said expanded cells exhibit an increased cytotoxicity as determined by in vitro cytotoxicity tests.

According to one embodiment of the described method, the serum is selected from the group consisting of human serum and autologous serum. The medium is supplemented with about 50 to about 1500 U/ml IL-2, about 1 to about 50 ng/ml anti-CD3-antibodies and about 1 to about 40% serum.

The agitation and heating is, according to another embodiment, performed under the following conditions: a temperature of about 36-40° C.; a $CO_2$ concentration of about 4.7-5.1%; and gentle rocking at a rate and angle permitting the cells to adhere to the surface of the closed cell system. The rocking is performed at a rocking rate of about 4-8/min and at a rocking angle of about 4-8°.

The expansion is preferably performed until the total number of cells has expanded at least about 10-fold or until at least about 50% of the expanded cell population comprises activated NK cells and NK-like T cells, respectively.

The cell sample used to expand said cells is preferably a sample of peripheral blood, cell lines, or cytokine stimulated peripheral blood. Most preferably the cell sample is a sample of peripheral blood mononuclear cells (PBMC's).

According to one embodiment of the method, the cell sample is collected from a healthy subject.

According to another embodiment, the cell sample is collected from a tumour bearing subject, preferably having a tumour selected from the group consisting of haematological tumours and solid tumours.

According to another embodiment, the cells predominantly consist of natural killer (NK) cells with the phenotype $CD3^-CD56^+$ The concentration of cells initially added to the closed cell system is preferably about $0.5 \times 10^6$ to about $2 \times 10^6$/ml growth medium.

In one embodiment of the invention, the method further comprises the step of adding per day a volume of the medium supplemented with serum and IL-2 corresponding to about 50% of the total culture volume and discarding about the same volume of growth medium/day from the closed cell system, wherein said step is performed when the total cell density has increased with at least about 50% of the initial cell density.

Preferably said step is performed when the total cell density has increased with at least about 300% from the initial cell density, but wherein about 75% of the total culture volume is exchanged.

Alternatively, said step is performed when the total cell density has increased with at least about 500% from the initial cell density, but wherein about 100% of the total culture volume is exchanged.

According to yet another embodiment, freely combinable with one or more of the above disclosed embodiments, the cells are incubated for at least about 10 days.

According to one embodiment the closed cell system is a pre-sterile bag.

According to another embodiment, the closed cell system is a bioreactor.

Another embodiment of the present invention is a suspension of natural killer (NK) cells with the phenotype $CD3^-CD56^+$ and NK-like T cells with the phenotype $CD3^+CD56^+$ exhibiting increased cytotoxicity.

Preferably these cells exhibit an increased cytotoxicity, as determined by in vitro cytotoxicity tests, compared to cells expanded in flasks.

In a suspension of natural killer (NK) cells with the phenotype $CD3^-CD56^+$ and NK-like T cells with the phenotype $CD3^+CD56^+$ according to the invention, at least 35%, and preferably at least 50% of the expanded cell population, comprises activated NK cells.

In the context of the present invention a bioreactor is a re-usable automatic chamber-system that may refer to any device or system that supports a biologically active environment. Within the scope of the described invention the term bioreactor refers to a device or system meant to grow cells or tissues in the context of cell culture. A non-limiting example of a bioreactor system is the Wave bioreactor system 2/10 from GE-Healthcare, but a skilled person will appreciate that there are alternative bioreactors available from other sources, or will be able to construct a bioreactor in which the inventive method can be performed.

In the context of the present invention a closed system is a cell-growth chamber system consisting of a central cell culture bag wherein cells can be efficiently and quickly proliferated ex vivo, without any further steps of passage.

The term "cytotoxicity" means the quality of being toxic to cells. Examples of toxic agents include chemical substances, or immune cells such as cytotoxic lymphocytes such as cytotoxic T cells, NK cells and NK like T-cells. NK cells and NK like T-cells stand out with their high cytotoxic capacity.

A skilled person can determine the cytotoxicity using available methods. One way of determining if cells exhibit an increased cytotoxicity is to use the in vitro analysis of cell mediated cytotoxicity against K562 cells using the standard 4 hour $^{51}Cr$-release assay. Alternatively, the degranulation assay can be used. Both these methods are disclosed in the attached examples.

In the content of the present invention the terms "activation" and "activated NK cells" refer to NK cells that have received an activating signal. Activated NK cells are capable of killing cells with deficiencies in MHC class I expression.

The term "simultaneous activation" of NK cells and NK-like T cells means the cells are activated substantially simultaneously, preferably in the same cell culture.

Given their strong cytolytic activity and the potential for auto-reactivity, natural killer (NK) cell activity is tightly regulated. In order to kill cells with a missing or abnormal MHC class I expression the NK cells need to be activated. NK cells must receive an activating signal which can come in a variety of forms, the most important of which are cytokines, Fc-receptors, activating and inhibitory receptors.

In the content of the present invention the term "cell expansion" relates to the culturing of cells that go through a series of cell division steps and thus expand the number of cells present in the culture. Thus, the term "NK cell expansion" relates to the culturing of NK cells that go through a series of cell division steps and thus expand the number of cells present in the culture. The term "expanded NK cells" relates to NK cells obtained through NK cell expansion. More specifically, in one embodiment the term "expanded NK cells" relates to a polyclonal group of chronically activated $CD3^-CD56^+$ cells as well as NK-like T cells with the phenotype $CD3^+CD56^+$, expanded in a specific cGMP grade environment and cGMP grade medium.

In the context of the present invention the term "effector cell" relates to a cell that performs a specific function in response to a stimulus such as cells in the immune system. In one embodiment effector cells are a type of lymphocytes that have cytotoxic capacity (i.e. they induce death of other cells). Another embodiment are lymphocytes actively engaged in secreting antibodies. Non-limiting examples of effector cells are NK cells, T cells and NK-like T cells.

DETAILED DESCRIPTION OF THE INVENTION

Figure 1A:
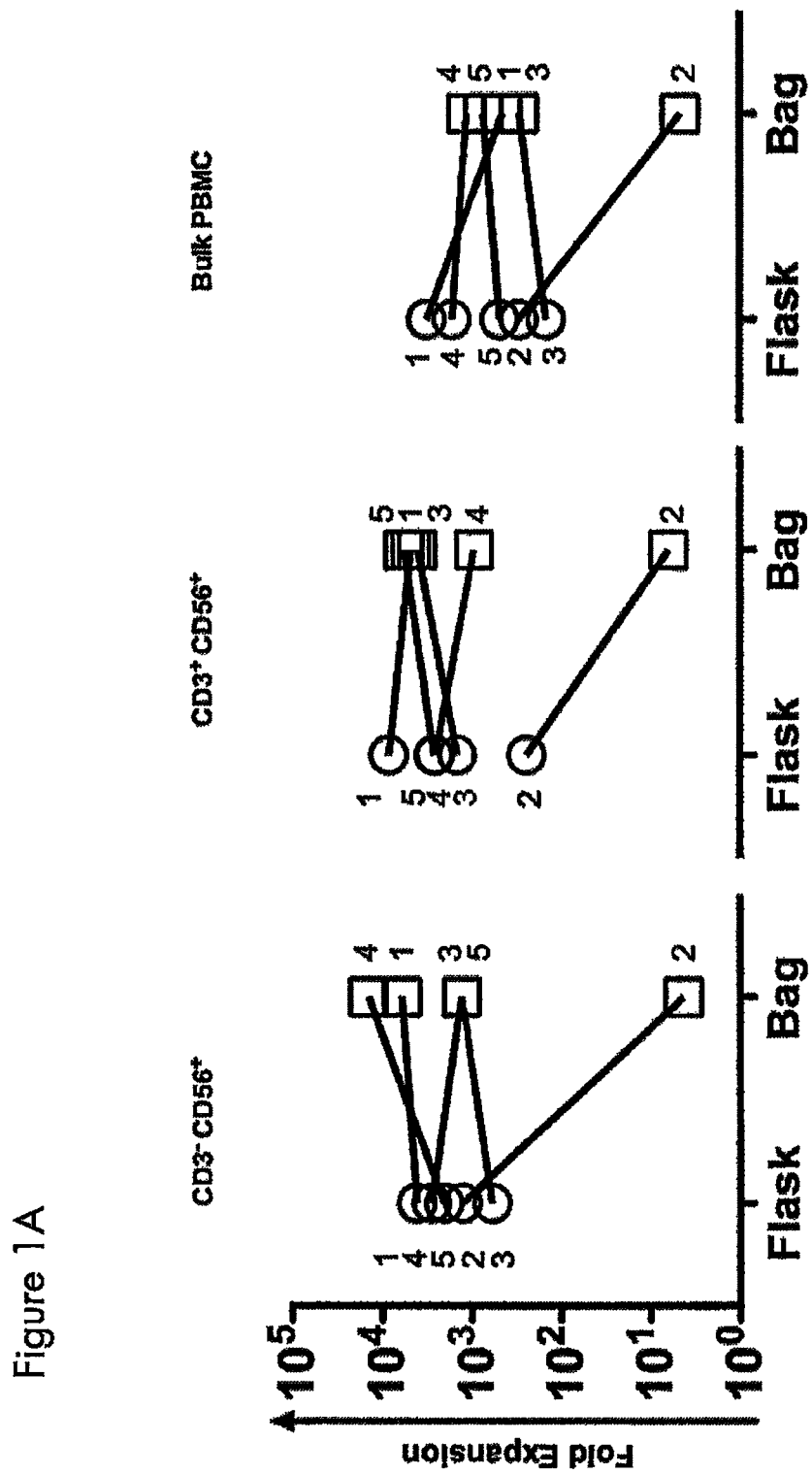
FIGS. 1A-D are diagrams showing a comparison of fold expansion in flask and bags (1A) and in flask and bioreactor (1B) and final product purity in flask and bags (1C) and in flask and bioreactor (1D).

Before the present invention is described, it is to be understood that the terminology employed herein is used for the purpose of describing particular embodiments only and is not intended to be limiting, since the scope of the present invention will be limited only by the appended claims and equivalents thereof.

If nothing else is defined, any terms and scientific terminology used herein are intended to have the meanings commonly understood by those skilled in the art to which this invention pertains.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

Ex vivo expansion and reinfusion of natural killer (NK) cells to patients afflicted with a malignant disease offers a new and potentially interesting therapeutic approach to combat such a disease. A prerequisite for this is the possibility to expand and use NK cells that meet the demands of clinical use. The present inventors have surprisingly been able to expand NK cells in a large scale for clinical applications. Thus, a GMP compliant automated closed culture system for preparation of large scale NK and NK-like T cell enriched effector populations that is applicable in clinical settings is provided.

As demonstrated in the examples below, the inventive method expands and activates NK cells having a satisfactory cytotoxic capacity (i.e. they induce death of other cells). The cytotoxicity of NK cells towards other cells can easily be measured, for example, by traditional cell counting before and after exposure to active NK cells. Such methods are well known to a person skilled in the art.

EXAMPLES

1. Ex Vivo Expansion of NK Cells and NK-Like T Cells from Peripheral Blood

Materials & Methods
Sampling and Isolation of Blood Mononuclear Cells (PBMCs)

Buffy coats, peripheral blood and apheresis products were obtained from healthy donors or MM patients via the blood bank at the Karolinska University Hospital, Huddinge. The experimental protocol was approved by the local research ethics committee.

The peripheral blood mononuclear cells (PBMCs) were isolated by gradient centrifugation, using Lymphoprep (Nyegaard, Oslo, Norway). PBMCs were washed twice with phosphate-buffered saline (PBS) (Gibco, Grand Island, N.Y., USA), and cell viability was assessed by trypan blue exclusion.

Growth Medium and Cell Counts

For all systems CellGro SCGM serum-free medium (CellGenix, Freiburg, Germany) with the addition of 5% human serum (Biowhittaker-Cambrex, Walkersville, Md., USA) and 500 U/ml rhIL-2 (Proleukin$^R$, Novartis Pharmaceuticals, East Hanover, N.J., USA) was used as growth medium. At the beginning of the culture, the medium was further supplemented with monoclonal anti-CD3 antibody (Orthoclone OKT-3, Ortho Biotech, Raritan, N.J., USA) at a final concentration of 10 ng/ml. Total cell numbers were assessed by staining cells with Trypan blue dye on days 0, 5-6, 9-10, 14-15, and 21 of culture. The final products were evaluated for safety, purity, and identity (cell viability and phenotype). Absolute cell counts were calculated by multiplying the total number of cells with the percentage of these subsets determined by flow cytometry (BD FacsCalibur; BD Biosciences, San Jose, Calif., USA).

Expansion in Cell Culture Flasks

The culture conditions for the expansion of cytotoxic cells in cell culture flasks have previously been optimized on PBMCs from healthy individuals (Carlens S. et al., 2001). In short, PBMCs were initially cultured in T25 flasks (TPP, Trasadingen, Switzerland) at a concentration of $0.5 \times 10^6$ cells/ml. After five days, the cultures were replenished with fresh medium with 5% human serum and IL-2 (500 U/ml) but without OKT-3, every 2-3 days until the end of the culture. To prevent contact inhibition of cell growth (Heiskala M. et al., 1987), the cells were transferred to bigger flasks (T75 or T150: TPP, Trasadingen, Switzerland) or passaged into multiple flasks when necessary. During medium replenishment, the cell concentration was adjusted to $0.5 \times 10^5$ cells/ml until day 10 and to $1 \times 10^6$ cells/ml after day 10. Occasionally, certain portions of the cells were frozen in order to keep the number of flasks manageable.

Expansion in the Wave Bioreactor System

The Wave Bioreactor is a cell culture system where the cells are grown inside a temperature and $CO_2$ controlled disposable, sterile bag that is placed on a rocking heated platform. The inventors have used a Wave Bioreactor System 2/10 (GE Healthcare, Somerset, N.J., USA). Our previous experience with this system has shown suboptimal efficiency when started in low volumes and low cell numbers. Yet, the amount of cells in peripheral blood samples of donors does not allow directly starting in the bioreactor. Therefore, in initial optimization experiments the inventors started the cultures in flasks and transferred the cells into the bioreactor around Day 5 when sufficient number of cells was reached. The bioreactor cultures at this day were started with $2 \times 10^6$ cells/ml in 800 ml.

In the final validation experiments, a whole unit of peripheral blood, or apheresis product from the donors was obtained and the cultures were initiated directly in bioreactors from day 0. The settings for the bioreactor were as follows at all times: Temperature 37° C., $CO_2$: 5%, Airflow: 0.1, Rocking rate: 6/min, Rocking angle: 6°. The cells were sampled and counted every other day and no further feeding was done until the cell density reached $3 \times 10^6$ cells/ml. From then on, the culture was fed with 500 ml of medium per day (50 ml/shot).

When the cells reached a density of 6×10⁶ cells/ml, the feeding was increased to 750 ml/day and after 1×10⁷ cells/ml, to 1000 ml/day.

Expansion in Vuelife™ Bags

Vuelife™ (American Fluoroseal Corporation, Md., USA) is a sterile cell culture bag made of fluorinated ethylene-propylene which is biologically, immunologically and chemically inert. It is highly permeable to gases and optically clear. The cultures in Vuelife bags were initiated with 5×10⁵ cells/ml in 60 ml medium using 72 ml Vuelife bags. The bags were incubated in a humidified incubator at 37° C. and 5% $CO_2$. Fresh medium was added every 2-3 days to adjust the concentration to 1×10⁶ cells/ml until day 10 and of 2×10⁶ cells/ml after day 10. Cells were split to bigger bags when necessary.

2. Analysis of Lymphocyte Subsets and Phenotyping by Flow Cytometry

Materials & Methods

The cell phenotype and percentage of subpopulations was analyzed by flow cytometry on days 0, 5-6, 9-10, 14-15 and 20 of culture using standard procedures with fluorochrome conjugated mAbs against CD3, CD14, CD19, CD45 and CD56.

In initial optimization experiments, Day 0 cells and day 20 cells from each expansion condition were subjected to a more detailed immunophenotypic analysis. To avoid inter-acquisition variability, all frozen samples were thawed simultaneously for a detailed phenotypic characterization of the NK cell subset by flow cytometry. This panel included fluorochrome conjugated mAbs against the following surface antigens: CD11a (HI111), CD3 (UCHT-1), CD7 (M-T701), CD14 (MOP9), CD16 (3G8), CD19 (HIB19), CD25 (M-A251), CD27 (M-T271), CD56 (B159), CD57 (NK-1), CD226 (DX11), NKB1 (DX9) and CD62L (DREG56) purchased from BD Biosciences, San Jose, Calif., USA; CD244 (2B4) (C1.7), NKG2D (ON71), NKp30 (Z25), NKp44 (Z231), NKp46 (BAB281), from Beckman Coulter Inc., Fullerton, Calif., USA; NKG2A (131411), NKG2C (134591), KIR2DL1 (143211), KIR2DL3 (180701) from R&D Systems, Minneapolis, Minn., USA.

All antibody stainings for flow cytometry were done according to the following protocol. The cells were washed once with PBS and incubated with appropriate amounts of antibody at 4° C. for 30 min. The labeled cells were then washed with PBS and fixed in 4% PFA prior to data acquisition. Data acquisition was done on a FACSCalibur (BD) or CyFlow ML (Partec GmbH, Munster, Germany) and data were analysed with CellQuest or FloMax software. For the analysis, appropriate SSC/FSC gates around the CD14⁻ CD19⁻ lymphocyte population were used. NK cells were gated as the CD3⁺CD56⁺ population. NK-like T cells and T cells were gated as CD3⁺CD56⁺ and CD3⁺CD56⁻ populations, respectively.

For each cell surface receptor analyzed, mean fluorescence intensity (MFI) values were calculated for day 0 and day 20 samples. To estimate the change in receptor expression, the inventors calculated MFI ratios ($MFI_{day20}/MFI_{day0}$) for each receptor. When the MFI for day 20 samples was higher than for day 0, the MFI ratio was higher than 1, which indicated the relative extent of up regulation in that receptor. Likewise, an MFI ratio below 1 was interpreted as down regulation in the expression of that receptor.

3. Evaluation of Cell Mediated Cytotoxicity

Materials & Methods

The cytotoxic capacity of the final product was evaluated in vitro with a standard 4 hour $^{51}$Cr-release assay against K562 cells (Aktas E. et al., 2009; Alter, G. et al., 2004). In short, K562 target cells were labeled with 100 μCi of $^{51}$Cr for 1 hour at 37° C., washed twice with PBS, and resuspended in RPMI medium. A total of 3×10⁴ target cells in 100 μl RPMI medium was placed in triplicates into V-bottomed 96-well plates and incubated for 4 hours with 100 μl of effector cells at appropriate concentrations to obtain effector:target ratios from 1:3 to 10:1. Aliquots of supernatants were counted using a Packard Cobra Auto-Gamma 5000 Series Counting System (Meridien, Conn., USA). The percentage specific $^{51}$Cr release was calculated according to the formula: percent specific release= [(experimental release-spontaneous release)/(maximum release-spontaneous release)]×100.

Analysis of NK Cell Degranulation

The expansion products were co-incubated with K562 target cells at a ratio of 1:1 in a final volume of 200 μl in round-bottomed 96-well plates at 37° C. and 5% $CO_2$ for 6 h. Fluorochrome-conjugated anti-CD107a mAb or the corresponding IgG1 isotype control was added at the initiation of the assay. After 1 h of coincubation, Monensin (GolgiStop, Becton Dickinson) was added at a 1:100 dilution. Surface staining was done by incubating cells with anti-CD3 and anti-CD 56 mAbs for 30 min on ice. The cells were then washed, resuspended in PBS and immediately analyzed by flow cytometry.

4. Statistical Analysis

Data analysis, preparation of graphs and statistical comparisons were done with the GraphPad Prism Software (GraphPad Software Inc. CA, USA).

Results

Evaluation of Cell Culture Bags and Bioreactor for NK Cell Expansion

Figure 1B:
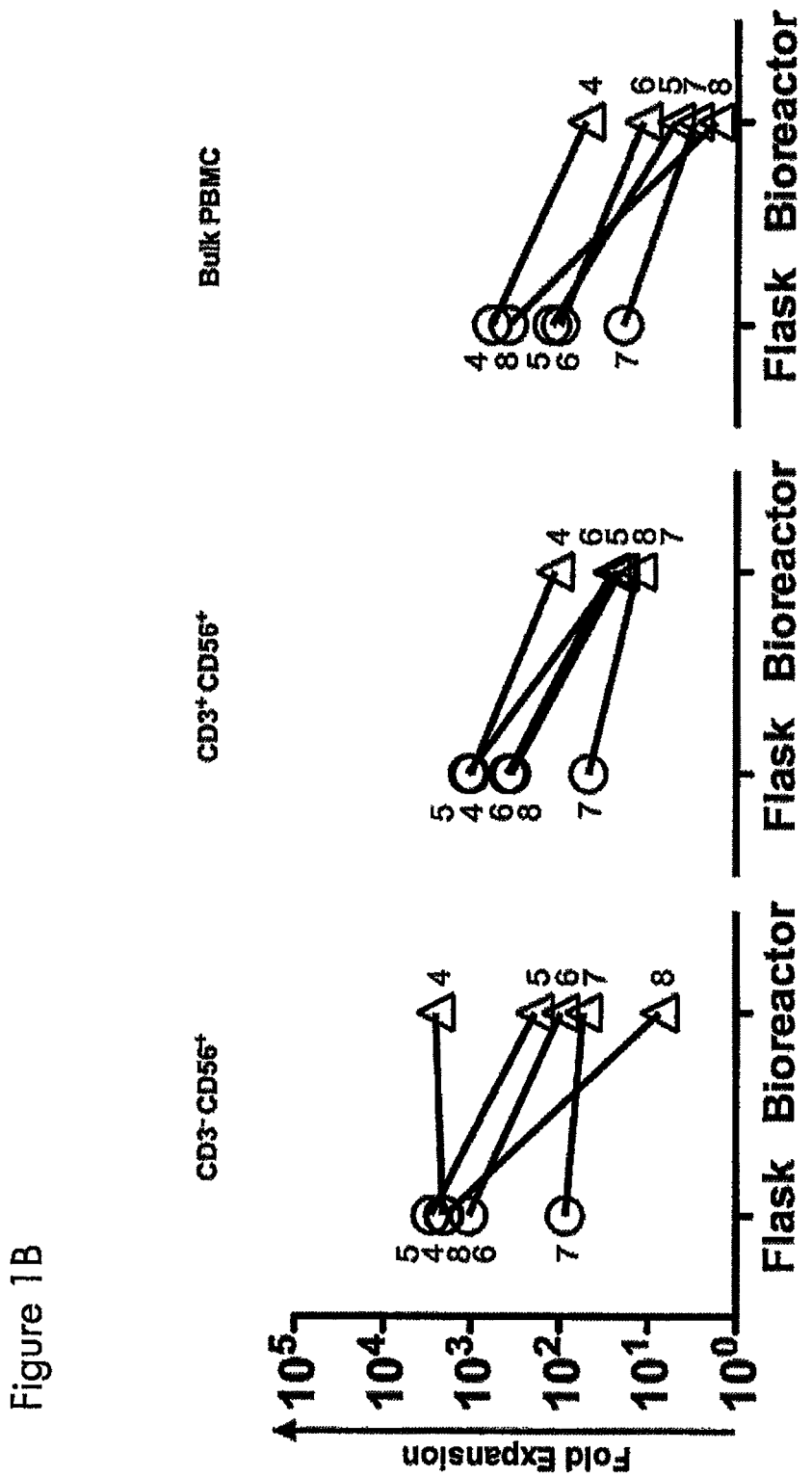
Figure 1C:
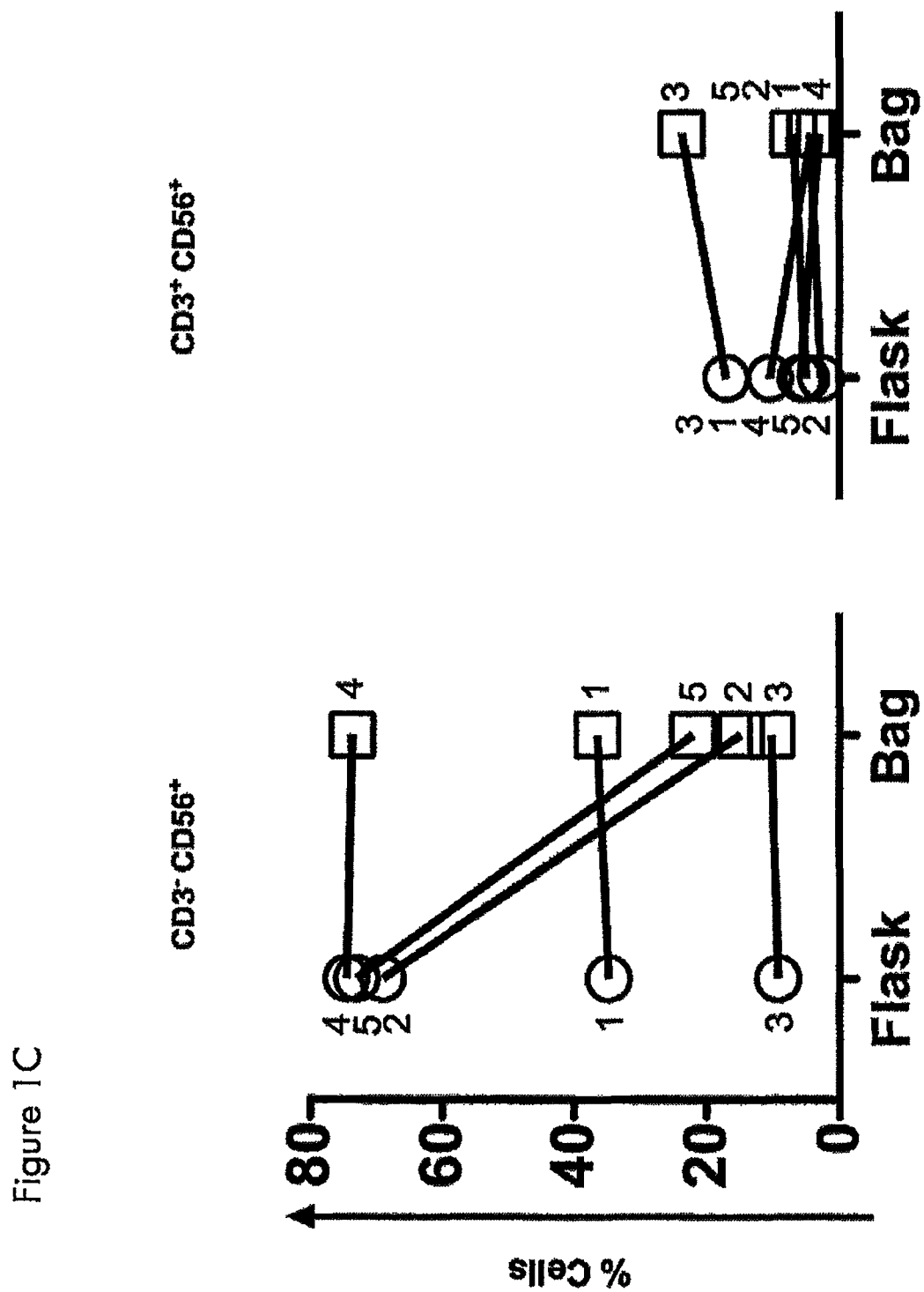

In an attempt to use a closed culture system for the expansion of NK cells, the inventors have initially compared cell culture bags with flasks using PBMCs from five healthy donors. FIG. 1A shows the fold expansion of bulk cells as well as NK and NK-like T cells from each donor, at the end of the expansion period. The mean bulk cell expansion was 530-fold in bags while the flask yielded a mean of 1100-fold expansion. The NK expansion in bags appeared impressive when compared to flask especially in three out of five donors. However, when the percentage of NK cells in the final product was taken into account (FIG. 1C), it was seen that expansion in bags does not correlate with expansion in flasks and might result in a lower NK cell purity at the end. The end product in bags had a mean of 31% NK cells while the mean NK percentage in the final product of flask was 53%.

Figure 1D:
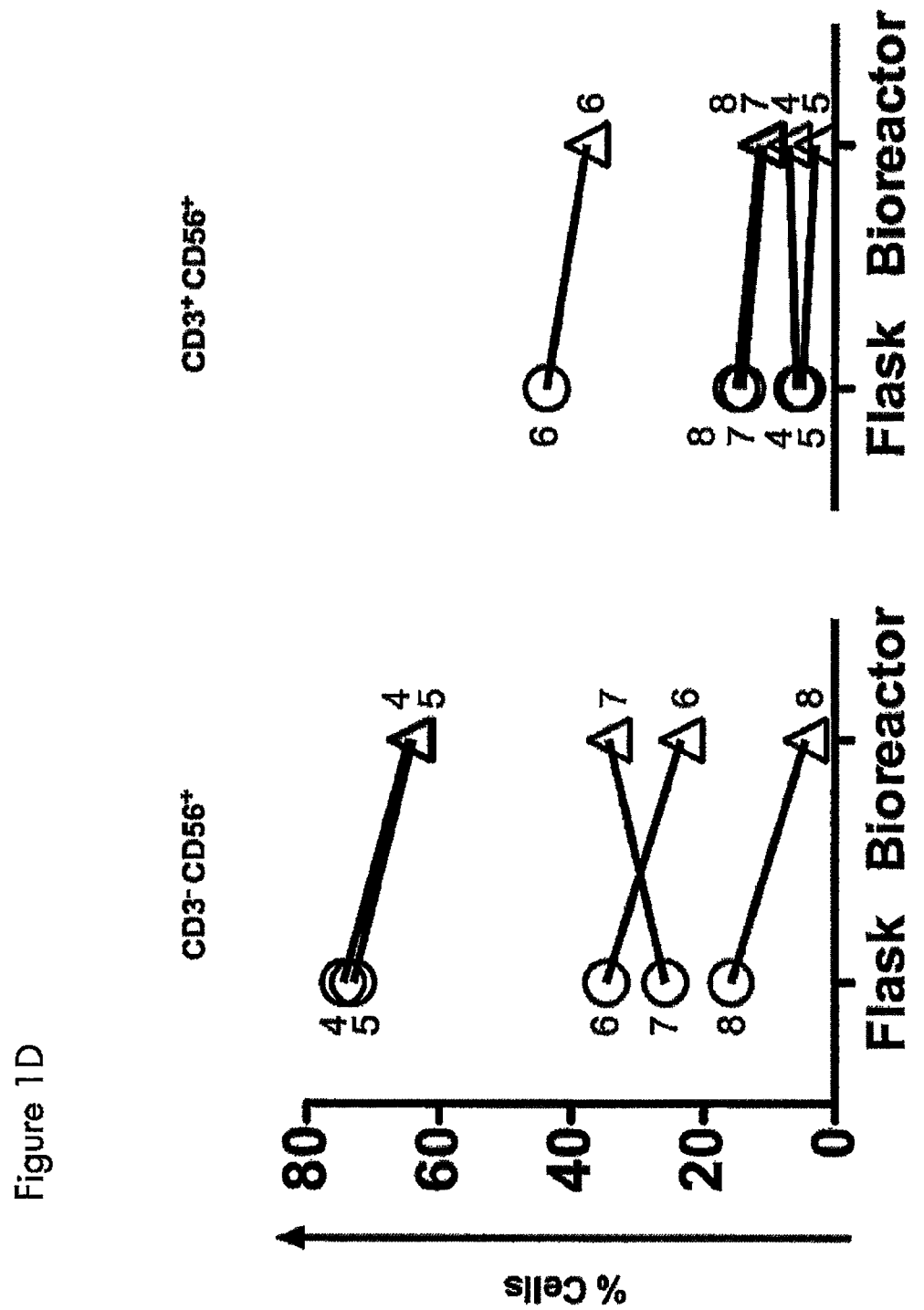

In search for a closed expansion system that results in comparable and correlating yield with flasks, the inventors have evaluated the use of an automated bioreactor system in comparison with expansion in flasks, using PBMCs from five healthy donors. The inventors have observed expansion of bulk cells (mean expansions: flask: 770-fold, bioreactor: 77-fold) while NK cells expanded preferentially and increased their share of the population in both conditions. Although fold expansions (FIG. 1B) of NK cells were lower than flasks in four out of five donors, percentages of these subpopulations in the final product were more comparable and correlating with flask expansion (FIG. 1D). The end product of the expansion protocols had a median of 38% NK cells in the bioreactor while there was 44% NK cells and 16% in flasks.

When compared with the previously mentioned results from bags, the percentage of NK cells in the bioreactor was higher than that in bags, even despite the fact that this set of donors had yielded a worse NK cell purity in flask expansion.

Taken together, the above results suggest that the fold expansion of NK cells is better in bags, whereas the purity is slightly higher in the bioreactor.

Due to the use of different donor sets and the high inter-individual variability in NK cell expansion, it was not possible to directly see the relative efficiencies of the bag and bioreactor systems. Owing to the fact that two of the five donors in these different groups were actually the same individuals (Donors 1 and 2), the inventors had a chance to directly compare the efficiency of expansion. Although it had a lower fold expansion rate, the bioreactor had a comparable percentage of NK cells in the final product (64%) when compared to flask (74%) which was higher than bags (47%). In the case of NK-like T cells, the percentages were very close to 5% in all three systems.

Figure 2A:
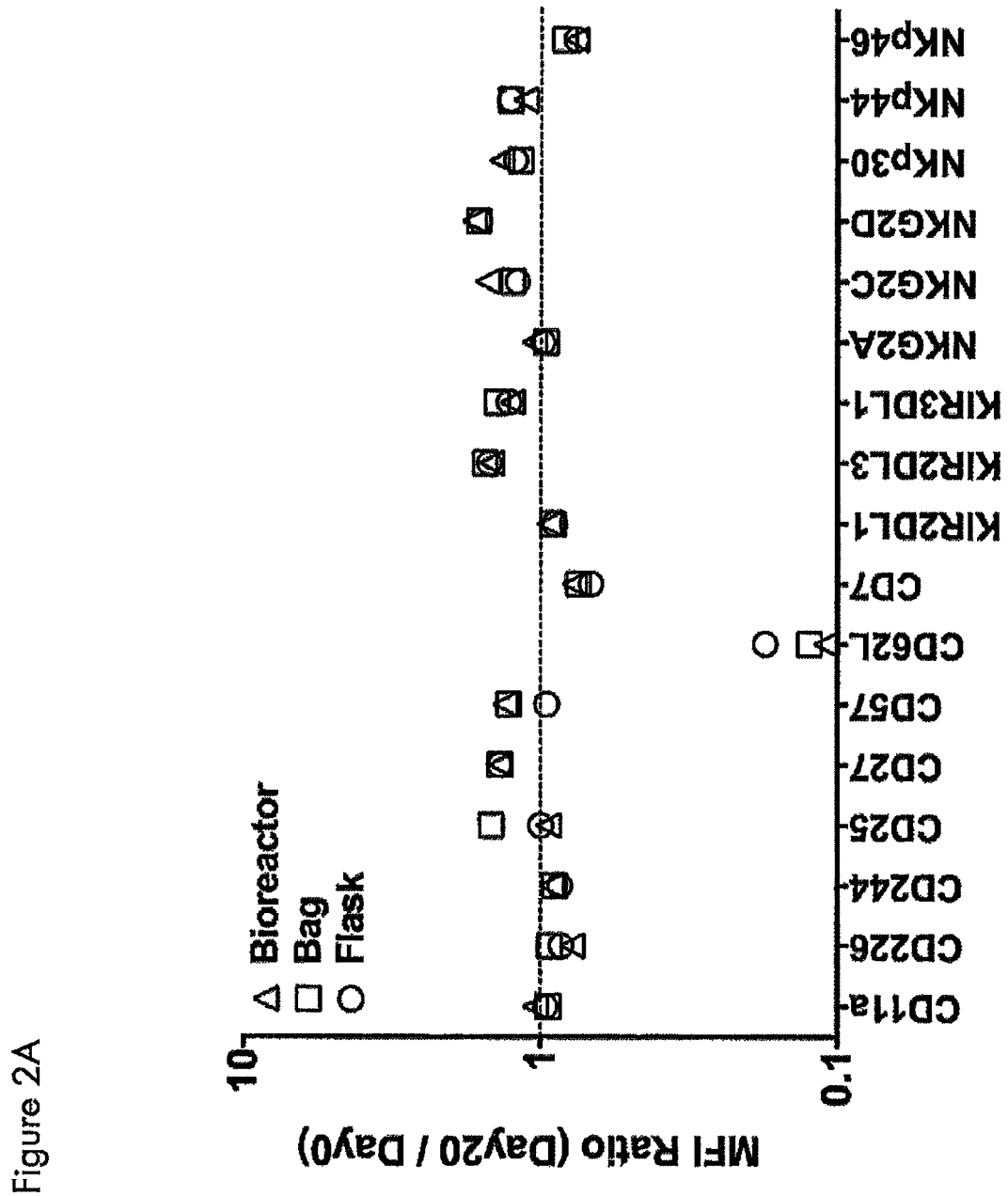
FIGS. 2 A-C are diagrams showing a comparison of phenotype (A and B) and cytotoxic activity (C) of the expanded cells following different expansion protocols.
Figure 2B:
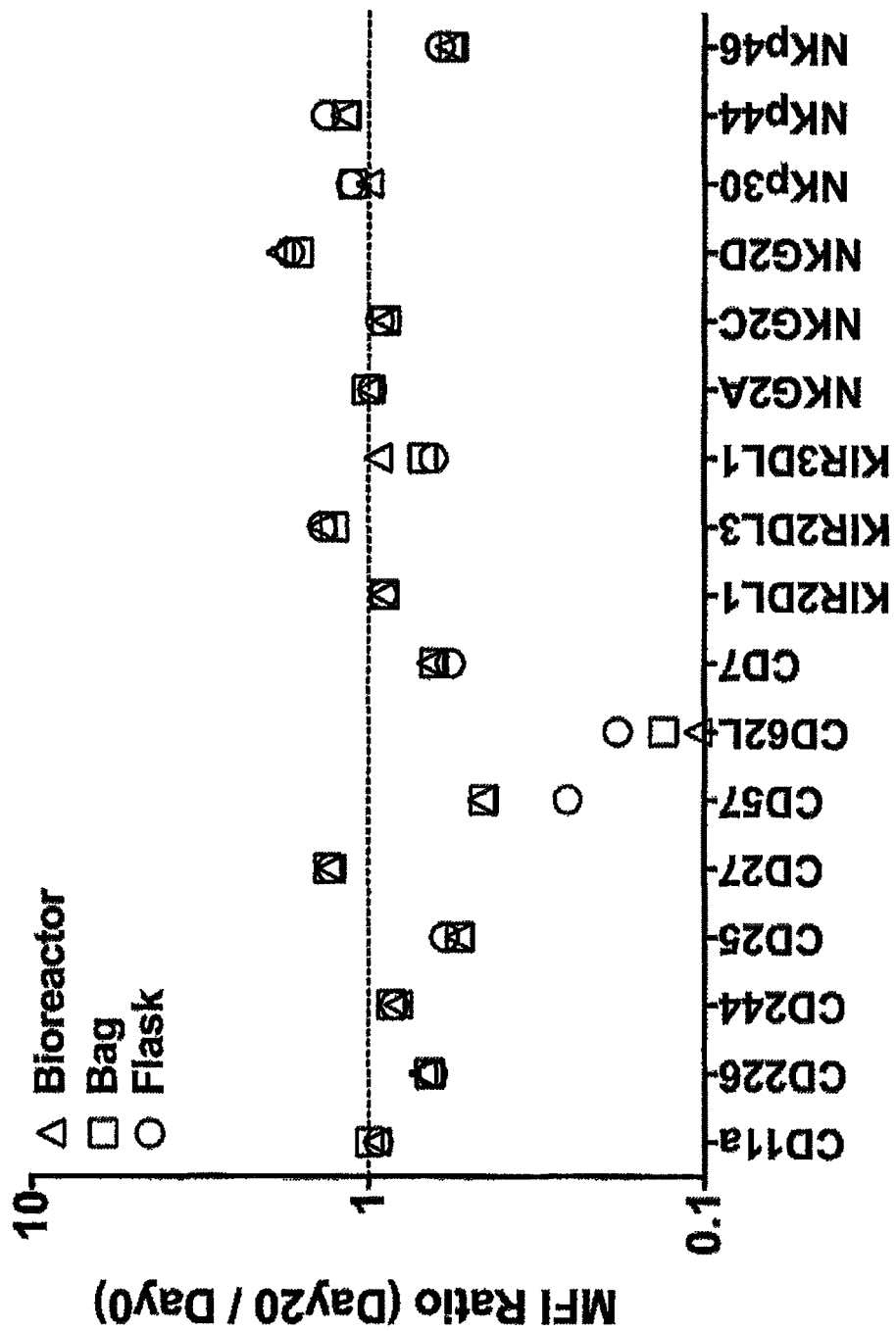

Expansion products from these two donors were subjected to further phenotypic analysis in order to see the pattern of change in receptor expression. Although there was an inter-individual variability as usual, the changes in receptor expression levels in the different final products were very similar (FIGS. 2A and 2B). It can be clearly seen that the extent of up- or down-regulation in a given receptor is the same no matter which culture protocol is used.

Figure 2C:
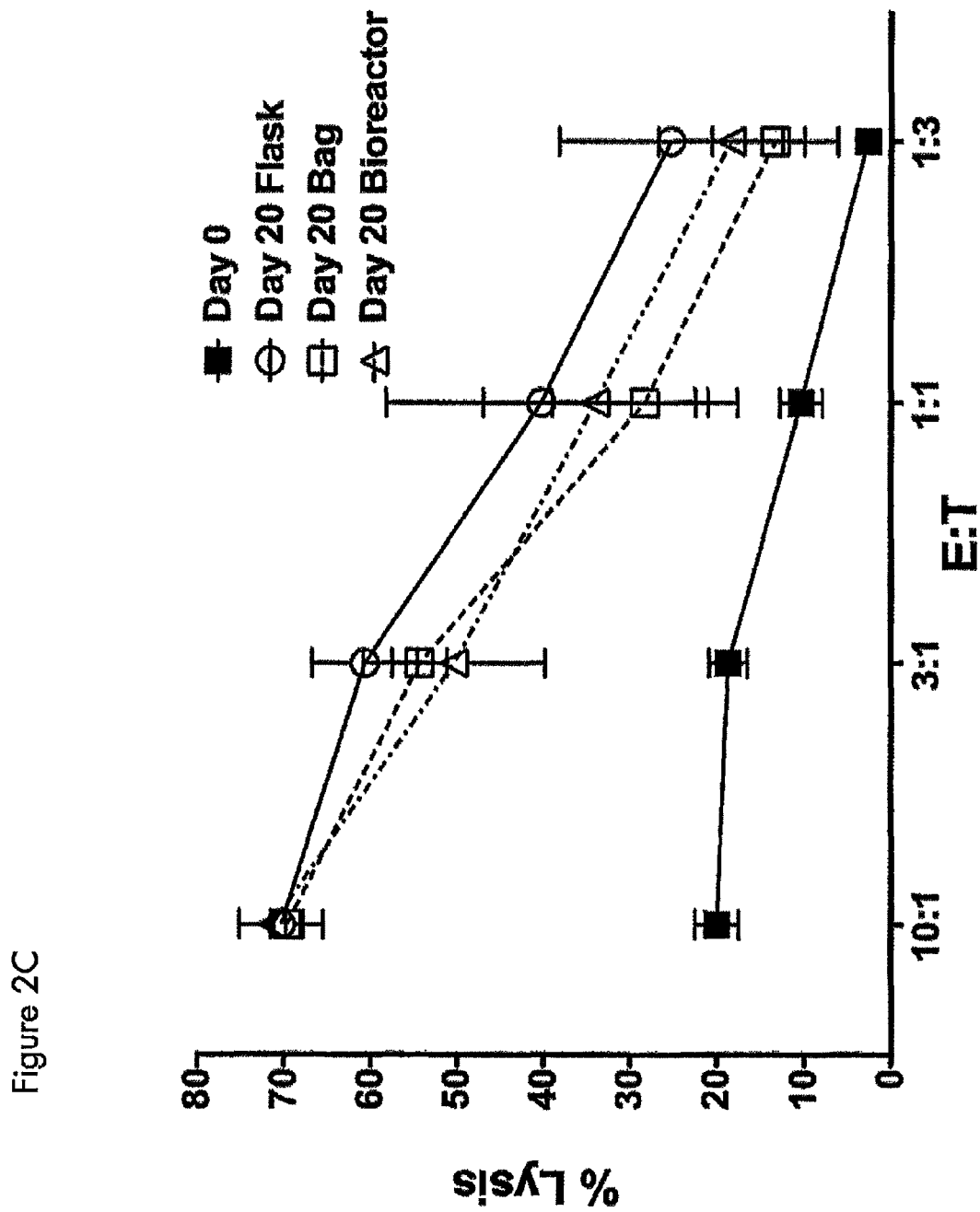

In order to clarify if the NK cells in the final products of different systems retain the same activation status and show comparable cytotoxicity, the inventors have evaluated the cytotoxic activity of the final products against the NK-sensitive cell line K562 (FIG. 2C). The inventors have observed no significant difference between the cytotoxic activities of cell preparations expanded under different conditions. These results ensure that the methods in question are all sufficient to produce cell preparations with increased cytotoxic capacity.

Validation of NK Cell Expansion Process in the Bioreactor

Figure 3A:
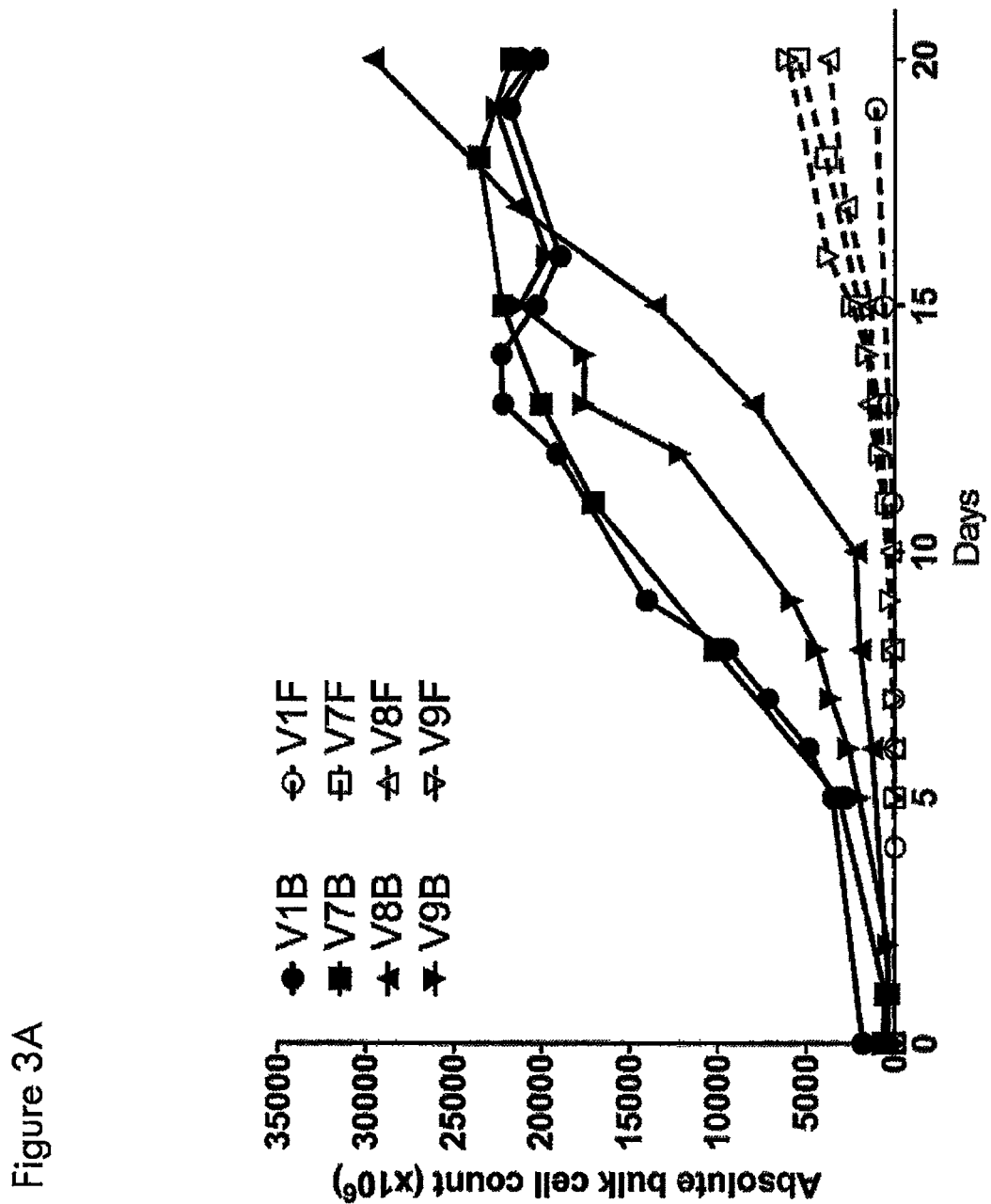
FIGS. 3 A-D are diagrams showing the expansion of cell cultures initiated in the bioreactor in comparison to flasks.
Figure 3B:
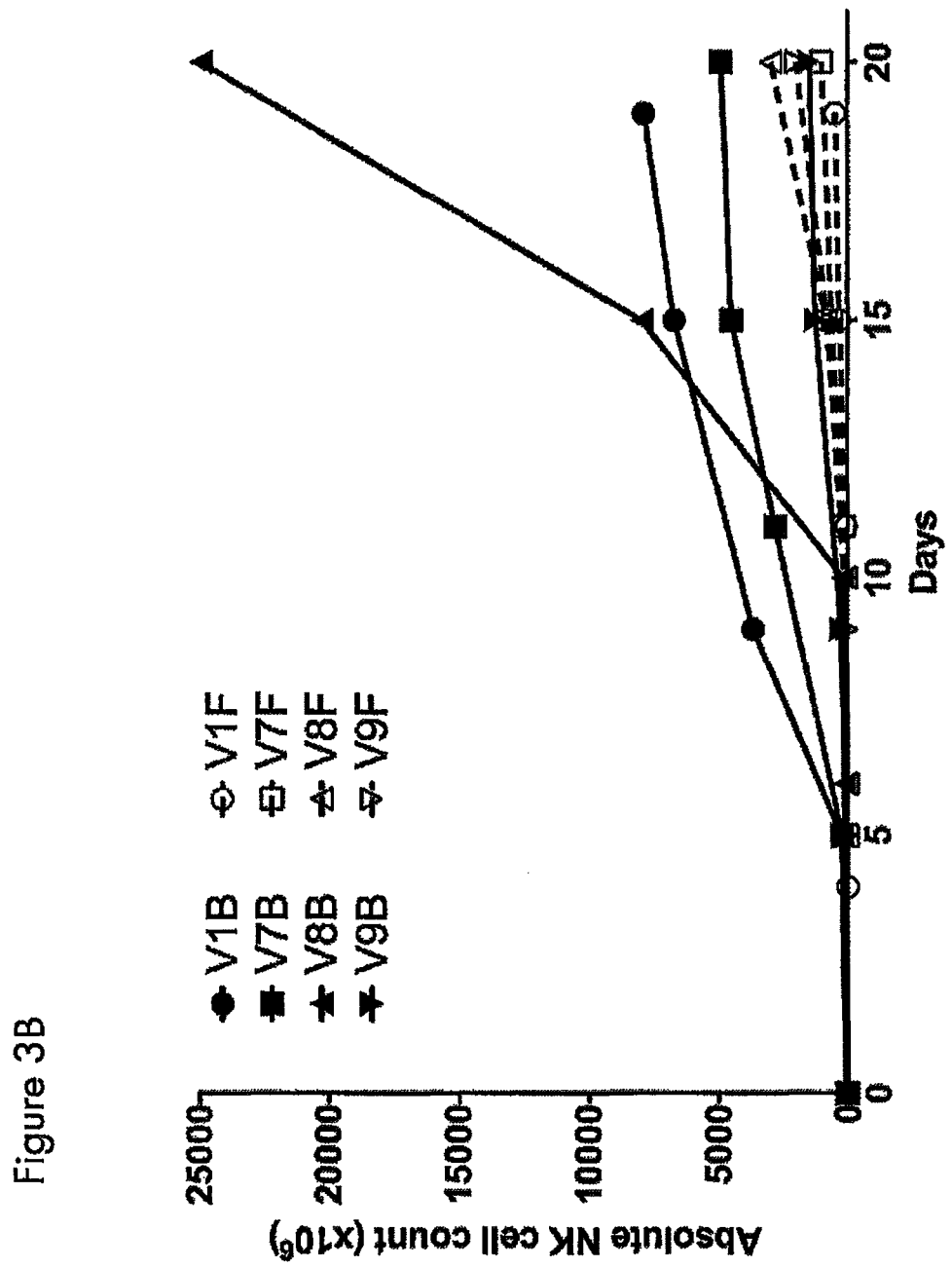
Figure 3C:
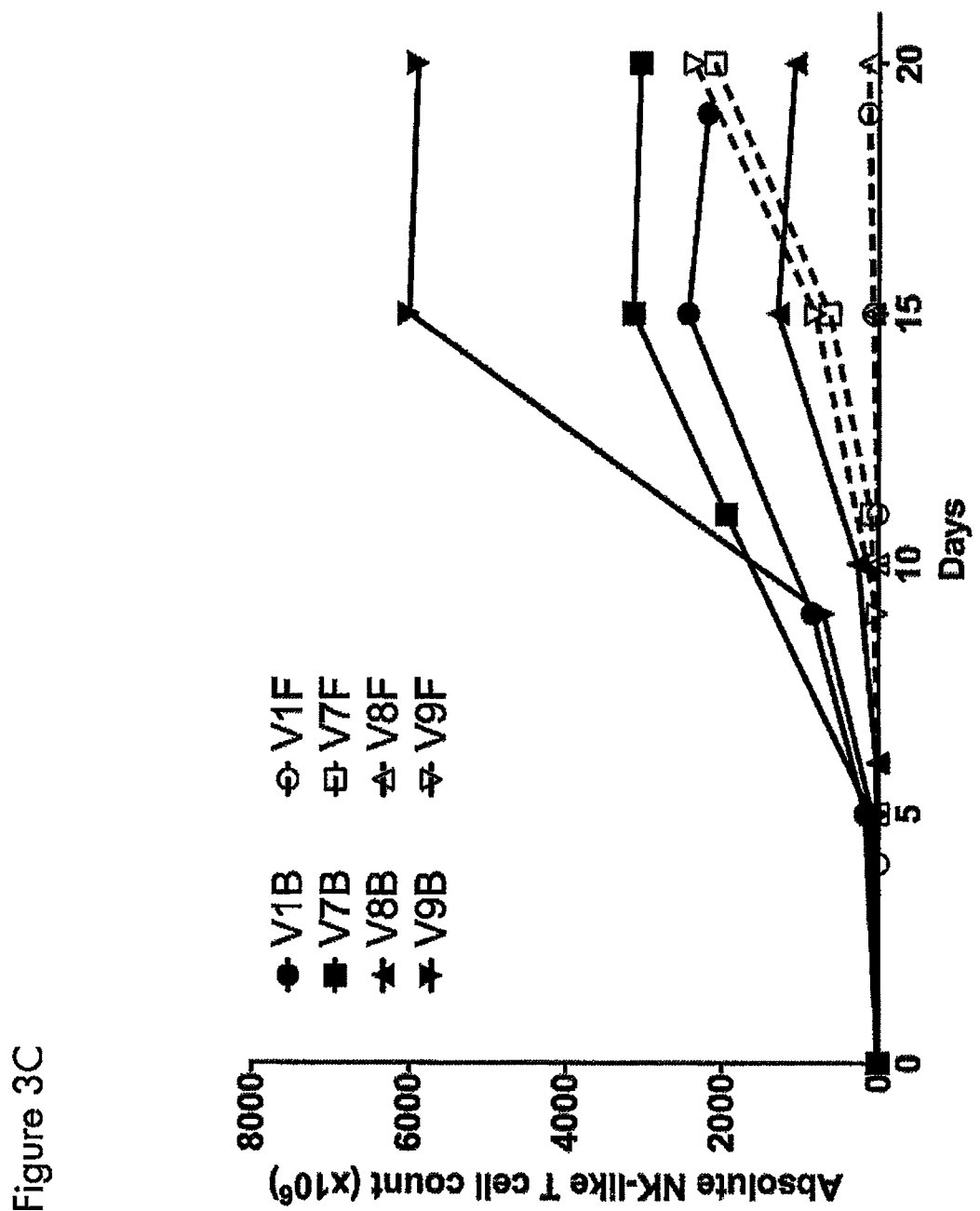

After demonstrating the feasibility of using the bioreactor for the expansion process, the inventors have continued with validation of the expansion process in bioreactor under cGMP conditions using apheresis products or whole-unit peripheral blood to initiate the culture directly in the bioreactor from day 0. PBMCs from two healthy donors and two MM patients were used for this validation process. For comparison purposes, the starting material, PBMCs, were expanded in parallel using flasks. FIG. 3 presents the expansion curves of bulk cells and lymphocyte subpopulations for all donors in bioreactor and flasks. The total number of cells reached was much higher in the bioreactor expansions, with an average purity of 37.5% while the purity was 43% in flasks. Although the NK cell purity was slightly lower in bioreactors, the final number of NK cells reached is impressive enough to facilitate clinical use of expanded NK cells in cancer immunotherapy settings.

NK Cells Expanded in the Bioreactor Display Higher Cytotoxic Capacity

Figure 4A:
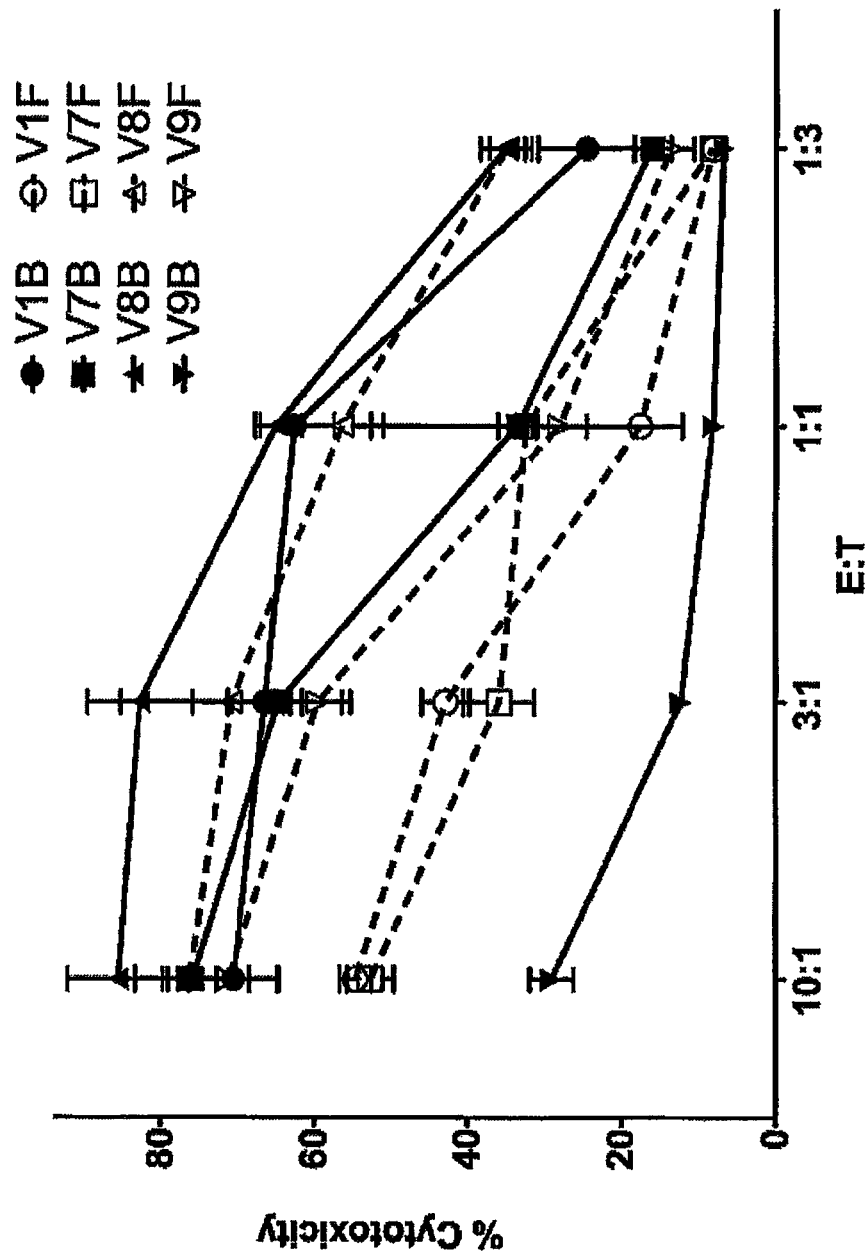
FIGS. 4 A-B are diagrams showing the functional comparison of cells expanded directly in bioreactors and flasks, respectively.
Figure 4B:
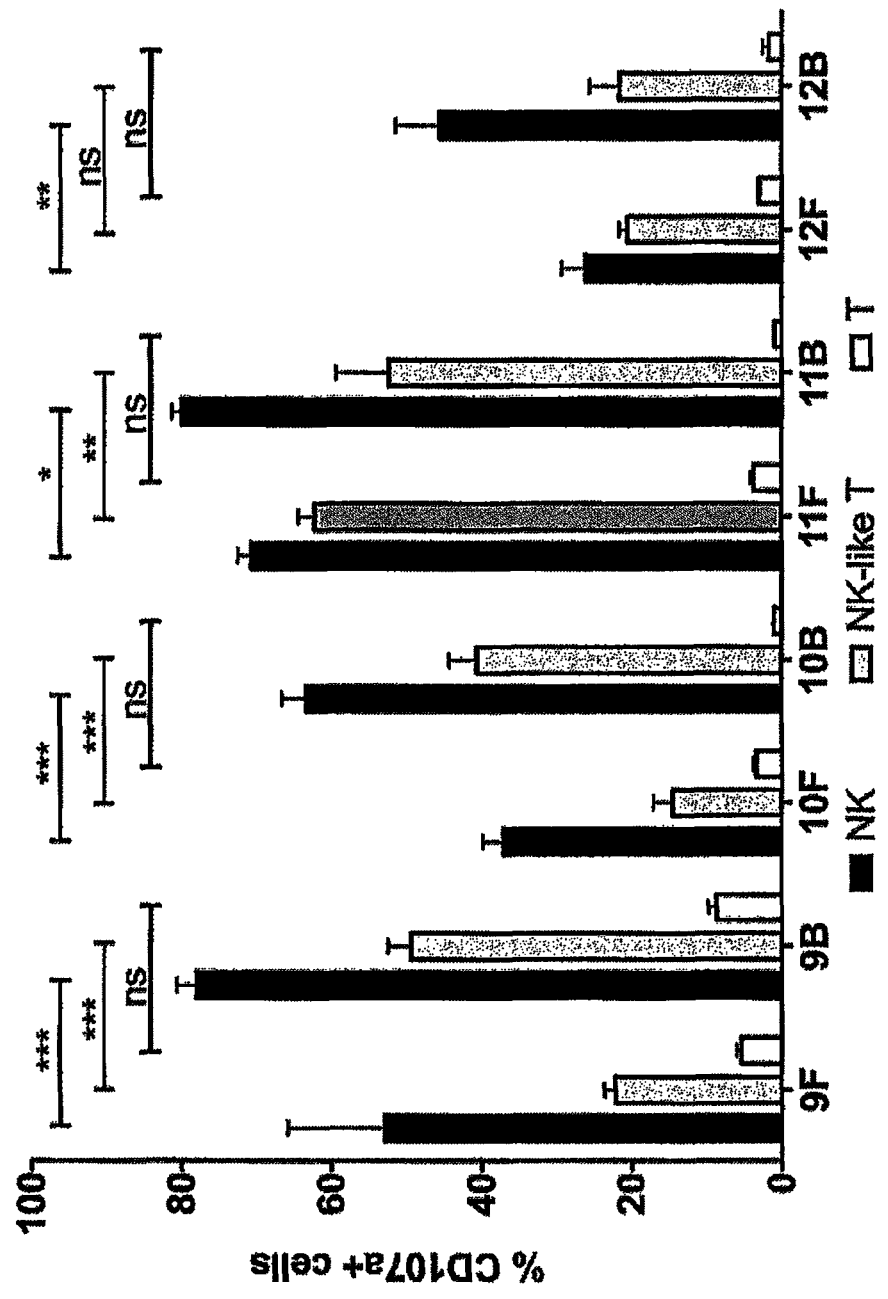

In previous experiments, where the expansion was initiated in flasks and subsequently transferred to bioreactors, the inventors had detected no difference in cytotoxic capacity or the phenotype of final products when compared to flask expansions. Interestingly, the inventors have observed that when expansion was initiated directly in bioreactors, the cytotoxic activity of the final product against K562 cells was remarkably higher when compared to the final product of flask expansions in 3 out of 4 donors (FIG. 4A). In order to better look into this phenomenon, the inventors have carried out degranulation assays against K562 cells, and measured the percentage of degranulating cells in each lymphocyte subpopulation (FIG. 4B). Surprisingly, the inventors have observed that the extent of degranulation observed in the NK cell fraction from bioreactor expansions was significantly higher than NK cells from flask expansions in all 4 donors. Likewise, the degranulation of the NK-like T cell fraction was significantly higher in 3 out of 4 donors. Taken together, these results suggest that the expansion process carried out in the bioreactor performs better in terms of elevating the cytotoxic capacity of NK cells.

Figure 5:
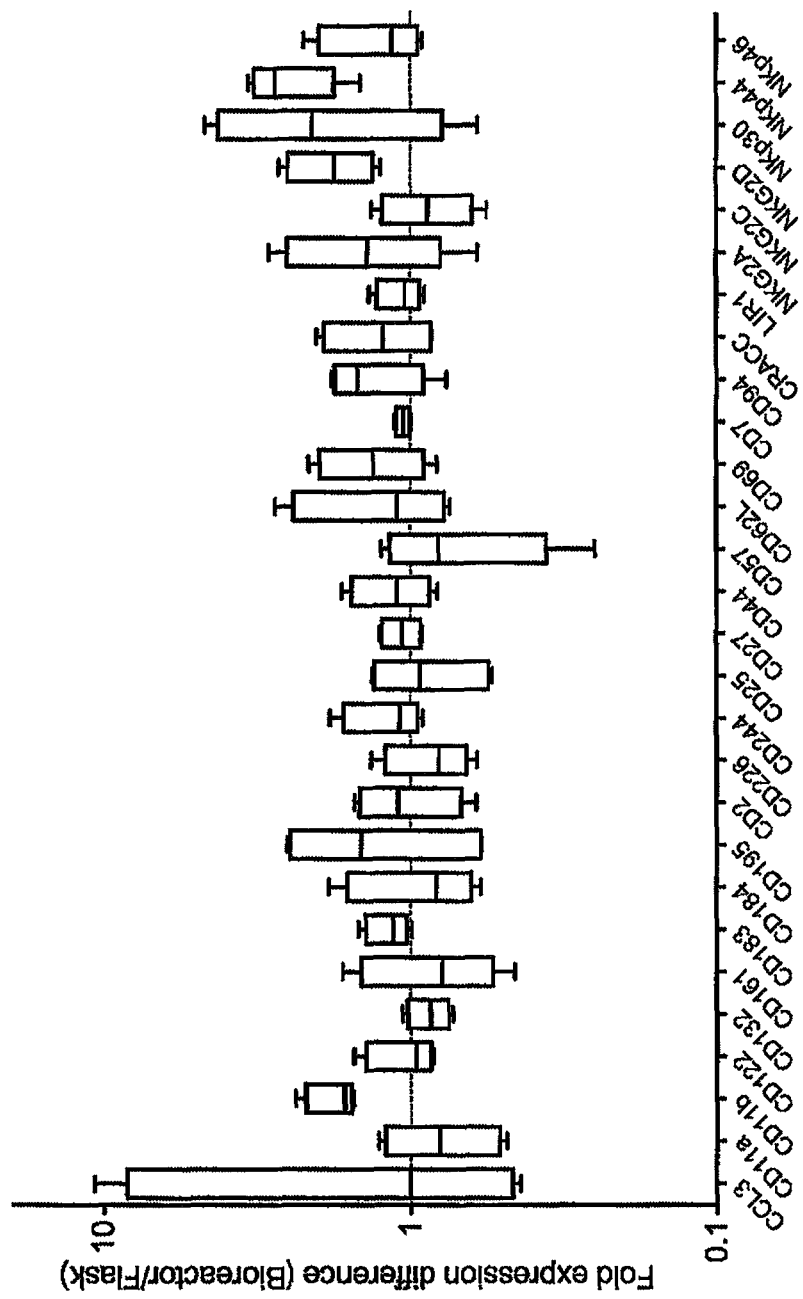
FIG. 5 shows the phenotypic comparison of NK cells expanded directly in bioreactor and flasks, respectively.

In an attempt to explain the difference in cytotoxic capacity of the final products from bioreactor and flask expansions, the inventors have performed detailed phenotypic characterization of the NK cells using multi-color flow cytometry. FIG. 5A shows the expression of various surface receptors on NK cells from bioreactor and flask expansions and summarizes the results from all donors and gives an overall picture of the phenotypic comparison between bioreactor and flask expansions. Overall, the NK cells in the final product look similar regardless of which expansion system is used, with slight but noticeable differences in the expression levels of CD11b, NKG2D and NKp44. Up regulation of NKp44 is one of the key factors in elevated cytotoxic capacity.

This study comparatively evaluates the use of cell culture flasks, bags and a bioreactor for the ex vivo expansion of NK and NK-like T cells originating from bulk PBMCs of human donors in an attempt to investigate the feasibility of producing GMP-quality effector cells in closed automated systems.

The inventors have previously reported a GMP-compliant culture medium which promotes the selective enrichment of activated NK cells in cell culture flasks (Carlens S. et al., 2001). Here, the inventors present the last step of optimizing a GMP quality automated closed culture system for preparation of large scale NK cell enriched effector populations that is applicable in clinical settings (Miller J S. et al., 1994; Luhm J. et al., 2002; Klingemann H G and Martinson J., 2004; Koehl U. et al., 2005) and/or use of feeder cell lines (Ishikawa E. et al., 2004; Torelli G F, et al., 2005) have been widely used for NK cell expansion in previous reports. In this study, the inventors do not utilize any separation steps but rather use bulk PBMCs for culture which results in a cell population enriched in NK cells that is distinct from LAK (Ramsdell F J and Golub S H., 1987) and cytokine-induced killer (CIK) cells (Chan J K. et al., 2006; Lu P H and Negrin R S., 1994) both in terms of NK cell content and anti-tumor activity (Bordignon C. et al., 1999).

The inventors have demonstrated that both bags and the bioreactor systems provide expansion of NK cells. An overall comparison of the expansion rates and end product purity between the two closed systems utilized in this study reveals that the bioreactor system provides sufficient amount of NK cells with higher purity and moreover has much less of T cells in the final product when compared to bags.

Surprisingly, the inventors have observed that NK cell activity is significantly higher in expansion products from bioreactors, as compared to those from flasks. Correlation of receptor expression levels with the response of NK cells against K562 has revealed that CD132, CD25, CD57 and NKG2C expression levels were inversely correlated with the response while expression levels of NKp30, NKp44 and NKp46 were directly correlated. Observing a reverse correlation with the expression of the activating NK cell receptor NKG2C is unusual but has very little meaning in this case, as the target K562 cells are known to lack the expression of it ligand HLA-E (Khalil-Daher I. et al., 1999). Statistical analysis of receptors correlating with NK cell response has revealed that NKp44 both correlates positively with response, and is expressed at a significantly higher level in bioreactor products when compared to flask expansions. This can, at least in part, explain the observation of high cytotoxic capacity of the bioreactor products. Unlike the other NCRs, NKp44 (Vitale M. et al., 1998) is expressed exclusively on activated NK cells and is upregulated after in vitro IL-2 stimulation (Biassoni R. et al., 2002). Therefore, in this case, it might be presenting as a surrogate marker of how well the IL-2 in the culture is being used and what the extent of activation in the NK cell population is. Thus, the elevated expression of NKp44 provides a functional significance to the expansion procedure being carried out in the bioreactor rather than conventional cell culture flasks.

Regarding practicalities, the inventors have observed that all systems in question have certain advantages and disadvantages. Expansion in cell culture flasks has the inherent risk of exposure to external agents and contamination. Although this risk is minimized in GMP laboratory environments, the use of closed automated systems is definitely preferred as long as it supplies sufficient amounts of cells. Initiation of culture in flasks does not demand a high number of cells but as the cells have to be kept within a certain concentration (Heiskala M. et al., 1987), splitting into new flasks during expansion ends up in an impossible number of flasks to handle. Culturing can also be initiated with few cells in small bags and results in good expansion but the purity of NK cells are lower than the other systems and the cells still need to be split into more than one bag. Yet, expansion in bags can be easily optimized in a standard cell culture laboratory, without the need to invest in additional equipment. More than one expansion can be carried out simultaneously using bags with the only limitation being incubator space, whereas the bioreactor needs extra investment for purchase of the machine and can be used for one expansion at a time.

The bioreactor is the most practical method, as it requires minimum hands-on time. However, the initiation of this system requires many cells and expansion rate is lower. The continuous rocking motion of the bioreactor ensures a dynamic and homogenous culture environment that provides many advantages such as uniform culture conditions, ease of sampling and better quality of control processes like the measurement of pH and dissolved oxygen. The use of such dynamic culture conditions is most probably a major factor contributing to the feasibility of growing cells more concentrated in the bioreactor. This avoids any waste of media or additional components, which dramatically decreases the overall cost of the process. Using the average expansion curves for each protocol, the inventors have estimated that, for acquiring similar number of NK cells, the bioreactor system uses approximately $\frac{1}{10}$ times the media components used for bags and $\frac{1}{25}$ times the media components used for flasks. The consumption of media and cytokines is even more (around 2.5 times of bags) in flasks.

Naturally, the use of a dynamic bioreactor system for ex vivo culture demands a number of factors to be evaluated carefully. Hematopoietic cells are relatively sensitive to shear and it is reasonable to assume that high shear processes are unsuitable for ex vivo expansion (Nielsen L K., 1999). Thus, stirred-tank bioreactors (Pierson B A. et al., 1996) or perfusion culture systems relying on external filters and high flow rate are unlikely to provide a high efficiency. In order to achieve the full benefit of a bioreactor, it would be desirable to use a low shear stress producing system with an internal perfusion filter for removing media (Nielsen L K., 1999) and the bioreactor system used in this study can meet these expectations.

Another factor to consider carefully is the material used in the culture environment. Only few materials can support the growth of hematopoietic cells efficiently and factors such as cleaning, sterilization and reuse significantly affect their performance (Laluppa J A. et al., 1997). Thus, the use of disposable and pre-sterilized suitable materials is preferred. Both the bags and the bioreactor system used in this study are suitable for production in this respect.

One difference observed was a slightly lower viability of cells in the final products of the bioreactor and bags cultures when compared to flasks. This is most probably due to the fact that the dead cells are being continuously washed away in the flask culture every 2-3 days when the medium is being changed while no such procedure is involved in the closed systems. Yet, it is always possible to utilize a GMP quality washing step at the end of the culture, prior to administration.

All systems in question have certain practical advantages and disadvantages. Expansion of NK cells in cell culture flasks has the inherent risk of exposure to external agents and contamination. Although this risk is minimized in GMP laboratory environments, the use of closed automated systems is definitely preferred as long as it supplies sufficient amounts of cells. Culturing in flasks can be initiated with very low number of cells but as the cells have to be kept within a certain concentration, splitting into new flasks during expansion ends up in an impossible number of flasks to handle.

Culturing can also be initiated with few cells in small bags and results in very good expansion but the purity of NK and NK-like T cells are lower than the other systems and the cells still need to be split into more than one bag. Expansion in bags can be easily optimized in a standard cell culture laboratory, without the need to invest in additional equipment. More than one expansion can be carried out simultaneously using bags with the only limitation being incubator space, whereas the bioreactor can be used for one expansion at a time.

In conclusion, the results presented here clearly demonstrate that large amounts of highly activated effector cells for possible use in adaptive immunotherapy settings can be produced in a closed culture system under GMP conditions.

Although particular embodiments have been disclosed herein in detail, this has been done by way of example for purposes of illustration only, and is not intended to be limiting with respect to the scope of the appended claims that follow. In particular, it is contemplated by the inventors that various substitutions, alterations, and modifications may be made to the invention without departing from the spirit and scope of the invention as defined by the claims.

REFERENCES

Aktas E. et al. Relationship between CD107a expression and cytotoxic activity. Cell Immunol. 2009, 254 pp. 149-54.

Alici E. et al. Autologous antitumor activity by NK cells expanded from myeloma patients using GMP-compliant components. Blood 2008, 111 pp. 3155-62.

Alter G. et al. CD107a as a functional marker for the identification of natural killer cell activity. J Immunol Methods. 2004, 294 pp. 15-22.

Barkholt L. et al. Safety analysis of ex vivo expanded NK and NK-like T cells administered to cancer patients: a Phase I clinical study. Immunotherapy. 2009, 1 pp. 753-764.

Biassoni R. et al. Human natural killer receptors and their ligands. Curr Protoc Immunol. 2002; Chapter 14: Unit 14 10.

Bordignon C. et al. Cell therapy: achievements and perspectives. Haematologica. 1999, 84 pp. 1110-1149.

Carlens S. et al. A new method for in vitro expansion of cytotoxic human $CD3^-CD56^+$ natural killer cells. Hum Immunol. 2001, 62 pp. 1092-8.

Chan J K. et al. Enhanced killing of primary ovarian cancer by retargeting autologous cytokine-induced killer cells with bispecific antibodies: a preclinical study. Clin Cancer Res. 2006, 12 pp. 1859-1867.

Grimm E A. et al. Lymphokine-activated killer cell phenomenon. Lysis of natural killer-resistant fresh solid tumor cells by interleukin 2-activated autologous human peripheral blood lymphocytes. J Exp Med. 1982, 155 pp. 1823-1841.

Guimaraes F. et al. Evaluation of ex vivo expanded human NK cells on antileukemia activity in SCID-beige mice. Leukemia. 2006, 20 pp. 833-839.

Guven H. et al. Expansion of natural killer (NK) and natural killer-like T (NKT)-cell populations derived from patients with B-chronic lymphocytic leukemia (B-CLL): a potential source for cellular immunotherapy. Leukemia 2003, 17 pp. 1973-80.

Heiskala M. et al. Mechanism of cell contact-mediated inhibition of natural killer activity. J Immunol. 1987, 139 pp. 1414-1418.

Ishikawa E. et al. Autologous natural killer cell therapy for human recurrent malignant glioma. Anticancer Res. 2004, 24 pp. 1861-1871.

Khalil-Daher I. et al. Role of HLA-G versus HLA-E on NK function: HLA-G is able to inhibit NK cytolysis by itself. J Reprod Immunol. 1999, 43 pp. 175-182.

Klingemann H G and Martinson J. Ex vivo expansion of natural killer cells for clinical applications. Cytotherapy 2004, 6 pp. 15-22.

Koehl U. et al. Ex vivo expansion of highly purified NK cells for immunotherapy after haploidentical stem cell transplantation in children. Klin Padiatr. 2005, 217 pp. 345-350.

Laluppa J A. et al. Culture materials affect ex vivo expansion of hematopoietic progenitor cells. J Biomed Mater Res. 1997, 36 pp. 347-359.

Lu P H and Negrin R S. A novel population of expanded human CD3+CD56+ cells derived from T cells with potent in vivo antitumor activity in mice with severe combined immunodeficiency. J Immunol. 1994, 153 pp. 1687-1696.

Luhm J. et al. Large-scale generation of natural killer lymphocytes for clinical application. J Hematother Stem Cell Res. 2002, 11 pp. 651-7.

Miller J S. et al. Large scale ex vivo expansion and activation of human natural killer cells for autologous therapy. Bone Marrow Transplant 1994, 14 pp. 555-62.

Nielsen L K. Bioreactors for hematopoietic cell culture. Annu Rev Biomed Eng. 1999, 1 pp. 129-152.

Pierson B A. et al. Production of human natural killer cells for adoptive immunotherapy using a computer-controlled stirred-tank bioreactor. J Hematother 1996, 5 pp. 475-83.

Ramsdell F J and Golub S H. Generation of lymphokine-activated killer cell activity from human thymocytes. J Immunol. 1987, 139 pp. 1446-1453.

Rosenberg S. Lymphokine-activated killer cells: a new approach to immunotherapy of cancer. J Natl Cancer Inst. 1985, 75 pp. 595-603.

Sutlu T and Alici E. Natural killer cell-based immunotherapy in cancer: current insights and future prospects. J Intern Med. 2009, 266 pp. 154-181.

Torelli G F. et al. Expansion of natural killer cells with lytic activity against autologous blasts from adult and pediatric acute lymphoid leukemia patients in complete hematologic remission. Haematologica 2005, 90 pp. 785-792.

Vitale M. et al. NKp44, a novel triggering surface molecule specifically expressed by activated natural killer cells, is involved in non-major histocompatibility complex-restricted tumor cell lysis. J Exp Med. 1998, 187 pp. 2065-2072.

U.S. Ser. No. 10/242,7881

The invention claimed is:

1. A method of obtaining expanded and activated natural killer (NK) cells with the phenotype $CD3^-CD56^+$ and NK-like T cells with the phenotype $CD3^+CD56^+$, said method comprising:

i) providing a cell sample of peripheral blood from a tumour bearing subject;

ii) isolating cells from said blood sample and re-suspending the cells in growth medium;

iii) adding the isolated cells to a closed cell culture bag bioreactor at a concentration of about $0.5 \times 10^6$ to about $2 \times 10^6$/ml of growth medium;

iv) incubating and expanding the cells in the bioreactor with rocking motion agitation and heating until at least 50% of the expanded cell population comprises activated NK cells and NK-like T cells; and v) harvesting said expanded cell suspension of activated NK-cells and NK-like T cells from said bioreactor, wherein said harvested expanded and activated NK-cells and NK-like T cells (1) exhibit an at least three fold increase in cytotoxicity compared to freshly isolated donor cells as determined by an in vitro cytotoxicity test with K562 cells as target cells at an effector to target cell ratio of 10:1, and (2) express NKp44 at an at least two fold higher level compared to activated natural killer cells with the phenotype $CD3^-CD56^+$ cells obtained from flask expansions.

2. The method of claim 1, wherein said growth medium is supplemented with serum, interleukin-2 (IL-2) and anti-CD3 antibodies.

3. The method according to claim 1, wherein the cell expansion is performed until the total number of cells has expanded at least about 10-fold.

4. The method according to claim 1, wherein the cell sample is a sample of cytokine stimulated peripheral blood.

5. The method according to claim 1, wherein the cell sample is a sample of peripheral blood mononuclear cells (PBMCs).

6. The method according to claim 1, wherein the cells are incubated for at least about 10 days.

7. The method according to claim 2, wherein the serum is selected from the group consisting of human serum and autologous serum.

8. The method according to claim 2, wherein the medium is supplemented with about 50 to about 1500 U/ml IL-2, about 1 to about 50 ng/ml anti-CD3-antibodies and about 1 to about 40% serum.

9. The method according to claim 1, wherein the tumour is selected from the group consisting of haematological tumours and solid tumours.

10. The method according to claim 1, wherein the obtained cells predominantly consist of natural killer (NK) cells with the phenotype $CD3^-CD56^+$.

11. The method according to claim 1, wherein the bioreactor is a wave bioreactor.

12. The method according to claims 1, wherein the rocking motion is at a rate and angle permitting the cells to adhere to the surface of the closed cell system.

13. The method according to claim 1, wherein the rocking is performed at a rocking angle of about 4-8°.

14. The method of claim 1, wherein the rocking is performed at a rocking rate of about 4-8 rocks per min.

15. The method according to claim 1, wherein the method is performed at a temperature of about 36 to about 40° C.

16. The method according to claim 1, wherein the method is performed at a $CO_2$ concentration of about 4.7 to about 5.1%.

17. The method according to claim 1, wherein the agitation and heating is performed under the following conditions: a temperature of about 36 to about 40° C.; a $CO_2$ concentration of about 4.7 to about 5.1%; and gentle rocking at a rate and angle permitting the cells to adhere to the surface of the closed cell system.

18. The method according to claim 1, wherein the agitation and heating is performed under the following conditions: a temperature of about 36 to about 40° C.; a $CO_2$ concentration of about 4.7 to about 5.1%; and at a rocking rate of about 4-8 rocks per min.

19. The method according to claim 1, wherein the agitation and heating is performed under the following conditions: a temperature of about 36 to about 40° C.; a $CO_2$ concentration of about 4.7 to about 5.1%; and at a rocking rate of about 4-8 rocks per min and at a rocking angle of about 4-8°.

20. The method according to claim 2, wherein the rocking motion is at a rate and angle permitting the cells to adhere to the surface of the closed cell system.

21. The method according to claim 2, wherein the rocking is performed at a rocking angle of about 4-8°.

22. The method of claim 2, wherein the rocking is performed at a rocking rate of about 4-8 rocks per min.

23. The method according to claim 2, wherein the method is performed at a temperature of about 36 to about 40° C.

24. The method according to claim 2, wherein the method is performed at a $CO_2$ concentration of about 4.7 to about 5.1%.

25. The method according to claim 2, wherein the agitation and heating is performed under the following conditions: a temperature of about 36 to about 40° C.; a $CO_2$ concentration of about 4.7 to about 5.1%; and gentle rocking at a rate and angle permitting the cells to adhere to the surface of the closed cell system.

26. The method according to claim 2, wherein the agitation and heating is performed under the following conditions: a temperature of about 36 to about 40° C.; a $CO_2$ concentration of about 4.7 to about 5.1%; and at a rocking rate of about 4-8 rocks per min.

27. The method according to claim 2, wherein the agitation and heating is performed under the following conditions: a temperature of about 36 to about 40° C.; a $CO_2$ concentration of about 4.7 to about 5.1%; and at a rocking rate of about 4-8 rocks per min. and at a rocking angle of about 4-8°.

* * * * *